Figure 1:
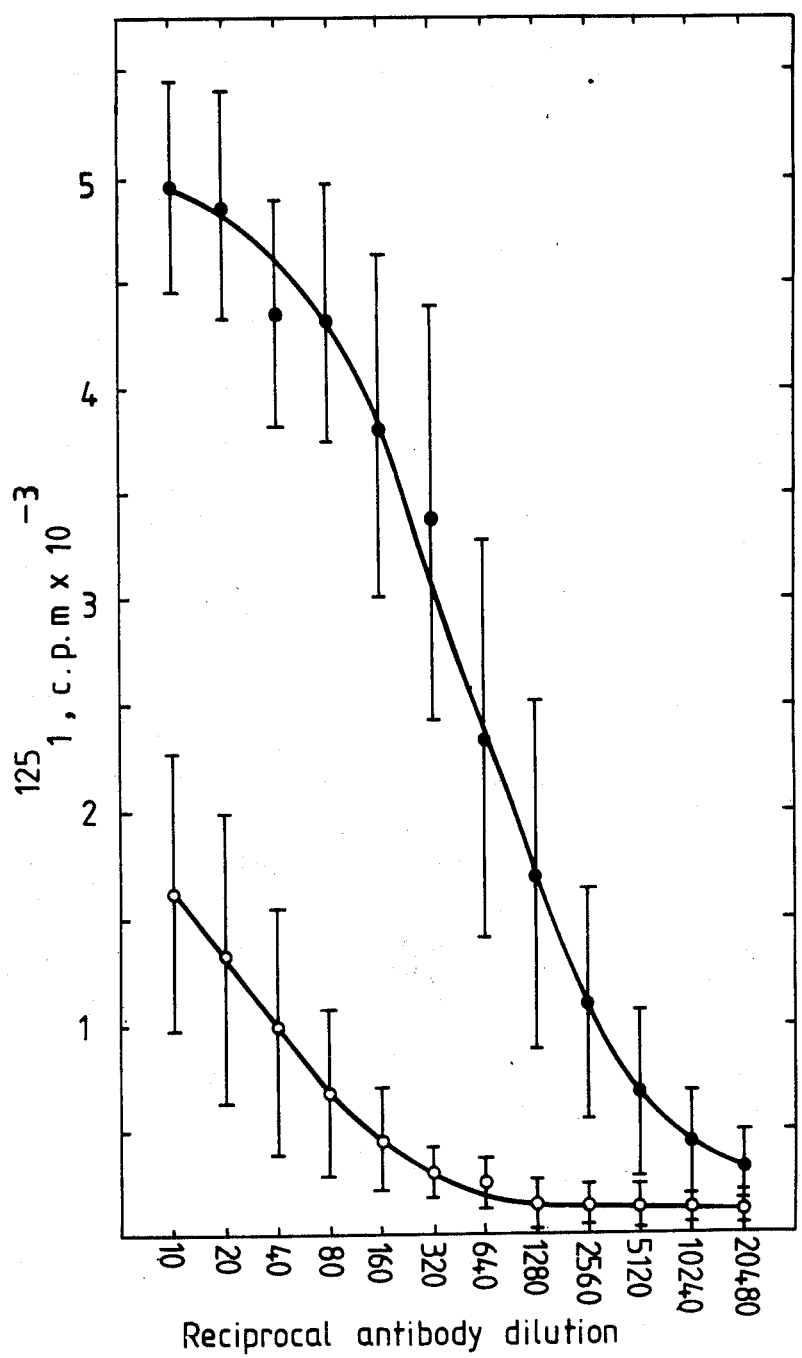

United States Patent [19]

Skelly et al.

[11] Patent Number: 4,666,713
[45] Date of Patent: * May 19, 1987

[54] RELATING TO HEPATITIS B VACCINE

[75] Inventors: Jacinta Skelly, Cardiff; Colin R. Howard, Tring; Arie J. Zuckerman, Hendon, all of England

[73] Assignee: National Research Development Corporation, London, England

[*] Notice: The portion of the term of this patent subsequent to Nov. 19, 2002 has been disclaimed.

[21] Appl. No.: 773,126

[22] Filed: Sep. 6, 1985

Related U.S. Application Data

[63] Continuation of Ser. No. 614,714, May 29, 1984, Pat. No. 4,554,157, which is a continuation of Ser. No. 341,142, Jan. 20, 1982, abandoned.

[30] Foreign Application Priority Data

Jan. 29, 1981 [GB] United Kingdom ................. 8102739

[51] Int. Cl.$^4$ ............................................. A61K 39/29
[52] U.S. Cl. ..................................... 424/89; 210/635; 210/656; 435/239; 530/380; 530/413; 530/809; 530/806; 530/826
[58] Field of Search .................. 424/89; 210/635, 656; 530/380, 413, 809, 826, 806; 435/239

[56] References Cited

U.S. PATENT DOCUMENTS 4,554,157 11/1985 Skelly et al. ........................... 424/89

OTHER PUBLICATIONS

McAleer et al, Nature, vol. 307, 1/12/84, 178-180.
Valenzuela et al, Nature, vol. 298, 7/22/82, 347-350.
Chanock et al, Cold Spring Harbor Laboratory, 1984, "Modern Approaches to Vaccines", pp. 245-250.

Primary Examiner—Howard E. Schain
Attorney, Agent, or Firm—Fleit, Jacobson, Cohn & Price

[57] ABSTRACT

Immunogenically active fragments of hepatitis B surface antigen, which are a glycoprotein of molecular weight about 28,000 (gp 28) and a protein of molecular weight about 23,000 (p 23), obtained by known methods by treatment of surface antigen with detergent, are prepared in micelle form substantially free from detergent. The micelles are at least as immunogenic as the unfragmented antigen from which they are derived and are useful in the preparation of hepatitis B vaccine. The detergent is removed by layering the detergent containing fragmentation product on an aqueous buffer containing a sucrose gradient and centrifuging the layered buffer when micelles containing both gp 28 and p 23 form and can be recovered in substantially detergent free form from the centrifuged layered buffer.

11 Claims, 1 Drawing Figure

RELATING TO HEPATITIS B VACCINE

This is a continuation of application Ser. No. 614,714 filed May 29, 1984, now U.S. Pat. No. 4,554,157 (which is a continuation of Ser. No. 341,142, filed Jan. 20, 1982 [abandoned]).

DESCRIPTION

This invention relates to hepatitis B vaccine and is particularly concerned with a process for the production of hepatitis B vaccine from fragments of hepatitis B surface antigen.

Virus hepatitis is a major public health problem in all parts of the world. The infection is caused by at least four different viruses of which hepatitis A and hepatitis B have been identified and characterised. A third form of hepatitis has recently been recognised and is believed to be caused by two viruses different from one another and from hepatitis A and B. Hepatitis B affects every field of medical practice throughout the world and it is the long-term persistence of this virus which causes particular problems, for example in the blood transfusion service. Hepatitis B virus can be transmitted directly through the skin so that the possible modes of entry are numerous.

The need for a vaccine to combat hepatitis B infection has been recognized for many years but traditional methods of vaccine production, by attenuation of the pathogenic virus by repeated passage through tissue culture have not proved possible because of the difficulty of growing this particular virus under artificial conditions. One alternative approach that has led to limited success in vaccine production has been the isolation and use of hepatitis B surface antigen alone. This surface antigen is essentially the protein coat of the virus which are usually spheres of protein 22 nm across. Experimental vaccines have been prepared from the plasma of healthy carriers of hepatitis B virus and it has been found that such a vaccine is capable of producing protective surface antibody and has led to protection in chimpanzee tests and in limited clinical trials.

One of the practical problems associated with the use of viral vaccines prepared from plasma is that, in addition to containing the desired antigenic material which provokes the production of the desired protective antibodies, the plasma derived vaccine contains numerous other antigenic materials which are all capable of provoking the production of other antibodies and the presence of such contaminating antigenic materials can lead to undesirable side-effects.

In an attempt to avoid the problems associated with these contaminating antigenic materials, attempts have been made to modify hepatitis B surface antigen (HBsAg) by breaking down the surface antigen into polypeptide fragements. Essentially, the fragementation of HBsAg was achieved by treating the HBsAg with the non-ionic detergent Triton X-100 by overnight incubation at 37° C. in the presence of a pH 7.3 buffer. The fragmented HBsAg was then passed through a Sepharose column so that the various fragments could be separated from one another. The molecular weight of the resulting fragments were determined by sedimentation techniques and the immunological properties of the resulting fragments were also examined. These tests showed that two of the resulting peptide fragments had significant hepatitis B surface antigen activity. These were a glyco polypeptide fragment having a molecular weight of about 28,000 and a polypeptide fragment having a molecular weight of about 23,000. This fragmentation of HBsAg has been described in more detail by Skelly, Howard and Zuckerman in J.Gen. (1979) 44 679–689.

While numerous tests were carried out on the glyco polypeptide fragment of molecular weight 28,000 and the polypeptide fragment of molecular weight 23,000 obtained as described above, to compare the immunogenicity of these fragments with the HBsAg from which they were derived, no satisfactory method was then available for the removal of all traces of the detergent which was used in the disruption of HBsAg and consequently, the fragments obtained by the procedure described in the Skelly et al paper mentioned above were unsuitable for the production of a clinically acceptable vaccine.

We have now found a method by which it is possible to remove substantially all traces of detergent from the immunogenically active fragments obtained by detergent disruption of HBsAg so that a clinically useful vaccine can be prepared.

Accordingly, the present invention provides a process for the production of a detergent free protein fraction, suitable for use in the formulation of a vaccine against hepatitis B virus infection, which comprises treating hepatitis B surface antigen with a non-ionic detergent to form a polypeptide mixture including an immunogenic glyco polypeptide fragment of molecular weight about 28,000 and an immunogenic polypeptide fragment of molecular weight about 23,000, introducing the polypeptide mixture to form a layer on top of an aqueous solution buffered to a pH which avoids denaturation of the glyco polypeptide of molecular weight about 28,000 and the polypeptide of molecular weight about 23,000, said aqueous buffer containing sucrose in a concentration gradient of at least 20% to not more than 65%, preferably not more than 50%, weight/volume, centrifuging the layered buffer and recovering from the upper part of the resulting buffer an aqueous fraction substantially free from detergent and containing micelles of the glyco polypeptide of molecular weight about 28,000 and the polypeptide of molecular weight about 23,000.

The process of the present invention may be used in relation to hepatitis B surface antigen of any origin e.g. of human or of chimpanzee origin.

The detergent used to treat the surface antigen will usually be an alkylaryl polyether alcohol such as one of the Tritons.

The process of the present invention preferably involves the use of a 20–50% or 20–60% w/v linear sucrose gradient in the aqueous buffer since it has been found that the use of such an aqueous buffer in which the sucrose concentration is stepped up in a linear manner across the range 20% w/v–50% or 60% w/v permits a substantially complete separation of the detergent from the immunogenically active glyco polypeptide of molecular weight about 28,000 hereinafter designated gp 28 and the polypeptide of molecular weight about 23,000 hereinafter designated p 23. The sucrose gradient technique also permits the generation of micelles from gp 28 and p 23. Such substantially detergent-free aqueous preparations avoid the problems of the known detergent containing materials from the clinical point of view and, furthermore, avoid the side-effect problems associated with the use of plasma-derived materials containing whole hepatitis B surface antigen.

The process of the present invention utilises an aqueous buffer which will maintain the pH of the aqueous medium at a value which avoids denaturation of gp 28 and p 23. As with most immunogenically active materials, the working pH range is about 4 to 8 and satisfactory results have been obtained with a pH of about 7.0 to 7.5. So-called TNE buffer, based on sodium phosphate, sodium chloride and ethylene diamine tetraacetic acid and having a pH of 7.4 has been found to be quite suitable for use in the present invention.

The layered sucrose gradient is centrifuged in accordance with the present invention to separate the detergent from the desired gp 28 and p 23 fragments. The exact speed of centrifugation is not critical but, in order to bring about separation in a reasonable period of time, we find it convenient to use speeds corresponding to a force of about 40 g to 250,000 g and usually, speeds corresponding to a force of at least 200,000 g will be used.

The time for which the centrifugation is carried out is again not critical but will depend upon the speed of rotation in the centrifuge, an adequate degree of separation of the desired immunogenic material and detergent normally being achieved within about six hours. To ensure that the detergent removal is as complete as possible, centrifugation will normally be carried out for longer than six hours and, as a practical matter, the centrifugation will normally be carried out for up to 24 or perhaps 48 hours.

In order to ensure uniformity of results, it is desirable to control the temperature during the centrifugation step although the particular temperature selected is not critical to the separation. There is normally no advantage to be gained by increasing the temperature above the ambient room temperature although, under some circumstances, it may be desirable to operate at slightly below room temperature. A practical working range is 4° to 20° C. although operation above 20° C. or below 4° C. is possible in accordance with the invention.

The process of the present invention produces a detergent free aqueous material, suitable as a clinical vaccine, containing micelles of gp 28 and p 23. To the best of our knowledge and belief, such detergent free aqueous preparations obtained by our procedure are new. Detergent free aqueous solutions containing micelles of gp 28 and p 23 and other material immunogenically similar to hepatitis B surface antigen derived from any other source such as cell lines or by genetic manipulation or synthesised chemically form a further aspect of the present invention.

The detergent free gp 28 and p 23 fragments may be formulated into clinical vaccines by methods known per se. For example, the immunogenic material may be formulated in a pyrogen free aqueous carrier containing about 5 to 50 μg per milliliter of the immunogenic material and such aqueous vaccines may also incorporate conventional vaccine adjuvants such as aluminum hydroxide or one of the organic adjuvants.

Vaccines containing the detergent free gp 28 and p 23 fragments obtained in accordance with the present invention have been found to be effective in both in vitro tests and in vivo tests in guinea pigs, mice and chimpanzees. The chimpanzee tests have shown that not only do vaccines obtained by the present invention generate high antibody titres in chimpanzees but also that they give an acceptable measure of protection when the immunised chimpanzee is challenged by the introduction of pathogenic virus into the animal.

The following Examples are given to illustrate the invention.

EXAMPLE 1

Hepatitis B surface antigen, obtained from the plasma of an infected chimpanzee, was purified in the form of 20 to 25 nm particles by the procedure described by Skelly et al (1978) J. Gen. Virol. 41 447–457. The resulting HBsAg was disrupted by overnight incubation at 37° C. in the presence of Triton X-100 and NaCl at final concentrations of 2% w/v and 0.5 M respectively as described in Skelly et al J. Gen. Virol. (1979) 44, 679–689. The solubilised material was passed through a column of concanavalin A Sepharose equilibrated in the complete disruption buffer supplemented with 1M $CaCl_2$ and MnCl. The fraction bound by the column was eluted with α-methylmanoside and was found to be the glyco polypeptide of molecular weight about 28,000 (gp 28) and the polypeptide of molecular weight about 23,000 (p 23).

The gp 28 and p 23 material were then separated from the detergent by layering on top of a linear sucrose gradient. The aqueous buffer used was a PNE buffer (0.05M tris HCl, 0.14M NaCl and 0.001M ethylene diamine tetraacetic acid) having a pH of 7.4. A linear sucrose concentration gradient was established in this aqueous buffer ranging from 20% w/v to 50 w/v. The detergent containing sample of gp 28 and p 23 was then introduced on top of the sucrose containing buffer and the liquid was then centrifuged in a Beckman SW40 centrifuge at 220,000 g for 24 hours at 4° C. 0.5 ml fractions were then collected from the top of the tube and the position of the polypeptide monitored by gamma spectrometry. Tests using iodine 125 labelled polypeptides showed that there was a peak approximately two-thirds of the way down the gradient. However, in control experiments in which the buffer contained 2% Triton the whole way through, the radioactivity remained at the top of the gradient showing that the use of a detergent free sucrose gradient was an effective way of separating the gp 28 and p 23 material from the detergent. The fact that the radioactivity peak was two-thirds of the way down the gradient, when the detergent free sucrose gradient was used in accordance with the invention shows that the gp 28 and p 23 materials reassociate to form polypeptide micelles which have an increased sedimentation coefficient compared to the immunogenic material in the detergent containing starting material.

Samples of the Triton free gp 28 and p 23 were incorporated into an aqueous buffer of the type described above in which a linear gradient of caesium chloride had been established at a concentration of 1.1 to 1.4 grams/$cm^3$. This material was centrifuged in the same Beckman centrifuge at 22,000 g for 24 hours at 4° C. and 0.5 ml fractions were then recovered from the top of the tube. Buoyant density determinations were made using an Abbé type refractometer which showed that the buoyant density was 1.25 g/ml compared with a density of 1.19 g/ml for intact HBsAg particles. Electron microscopy showed that the micelles of gp 28 and p 23 were pleomorphic and fluffy in appearance with a mean diameter of 120 nm. The micelles could be aggregated by rapid anti-HBs. Polyacrylamide gel electrophoresis showed that both gp 28 and p 23 were present in the micelles in the same proportion as in the detergent solution indicating that the micelles were not formed preferentially from one or other of the polypeptides.

RECOVERY OF SEROLOGICAL ACTIVITY

Specific HBsAg activity was monitored by reverse passive haemagglutination (RPHA) on the gp 28 and p 23 material and also on the HBsAg material after disruption with Triton and on the eluate from the Con-A-Sepharose. In one experiment in which 10 mg of HBsAg was disrupted, 3.4 mg was recovered from the Con-A-Sepharose column and 2.5 mg protein was recovered from the sucrose gradient representing 73% of the amount of gp 28 and p 23 originally present. The RPHA titre per milligram of protein was found to be $2.2 \times 10^3$ for the protein micelles formed in the sucrose gradient compared to $3.7 \times 10^5$ for the eluate from the Sepharose and $9.9 \times 10^4$ for the HBsAg after disruption with Triton.

IMMUNOGENICITY OF THE MICELLES OF GP 28 AND P 23

The immunogenic properties of the micelles obtained by the present invention and of the intact 22 nm HBsAg particles from which the micelles were obtained, were compared using a mouse potency test. The two preparations under test were first dialysed against a 0.1M phosphate buffer (PBS) of pH 6.6 and then made up to a final concentration of 200 µg protein per ml. In this phosphate buffer, 1 ml of a 2% suspension of the aluminum phosphate was added to 6 ml of each sample and absorption of the protein was carried out by mixing the suspensions overnight. The aluminum phosphate was then centrifuged and washed once with PBS. Measurements of protein and serological activity by reverse passive haemagglutination of the supernatants showed that more than 95% of the antigen had been absorbed on aluminum phosphate. The precipitate was then resuspended in PBS to give a final aluminum phosphate concentration of 0.04%. The suspensions were then diluted approximately with 0.4% aluminum phosphate in PBS in order to make both the volume and the aluminum phosphate content of the inocula the same for all antigen doses. Batches of 6 mice per dose were injected intraperitoneally with 20, 10 or 5 µg of either the intact 22 nm particle or the micelle of gp 28 or p 23 material in 100 µl volumes. Two booster doses were given at weekly intervals. The mice were bled 11 days after the last inoculation and the titres of antibody in the sera determined.

FIG. 1 of the accompanying drawings show protein A-radioimmunoassay of anti-HBs in sera of mice inoculated with three 10 µg doses of either the micelle formulation of the invention (shown as •) or a formulation of the intact 22 nm particle HBsAg (shown as o). The sera were initially diluted 1:10 in phosphate buffer saline (PBS) containing 0.5% bovine serum albumen (BSA) and serial two-fold dilutions were mixed with $^{125}$I-HBsAg (the intact 25 nm particles, 10 µl 24,000 cpm) and incubated overnight at room temperature. Protein A Sepharose (5% in PBS-BSA) was then added and the samples shaken vigorously 1 hour at room temperature. The Sepharose was pelleted by low speed centrifugation and the pellets and supernatant separated prior to counting. The points on FIG. 1 show the mean counts per minute associated with the precipitated immune complexes from six sera and the vertical lines show the standard deviation.

As shown in FIG. 1 there was consistently higher antibody levels in all the mice inoculated with the micelle preparation at the test dose level. Similar high antibody level were observed with other dose levels of the micelle preparation.

EXAMPLE 2

Surface antigen was isolated as 22 nm particles from persistently infected chimpanzee serum by the Skelly et al (1978) method mentioned in Example 1 and was disrupted substantially as described in Example 1 using slight modifications from the Skelly et al (1979) procedure mentioned. The 0.01M-tris-HCl pH 7.3 buffer contained a final Triton X-100 concentration of 2% w/v and the supplements in the buffer used for equilibration of the Concanavalin A Sepharose were 1mM $CaCl_2$ and 1mM-$MnCl_2$. The suspension was gently mixed on a rotator for 60 minutes and then packed in a $1 \times 10$ cm column and washed with buffer to remove unbound material. Bound material was eluted with 0.01 M-tris-HCl, pH 7.3 containing 2% TX-100, 0.5M NaCl and 5% α-methyl-D-mannoside (α-mm). Peak fractions were then centrifuged on 20–60% w/v linear sucrose gradients (free from detergent) in TNE buffer (0.5 M tris-HCl, pH 7.4, 0.14 M NaCl, 0.001 M EDTA) at 220,000 g for 24 hours at 15° C. in a Beckman SW40 rotor. The position of the desired gp 28 and p 23 fractions in the sucrose gradient was identified as explained in Example 1 and Triton-free samples of gp 28 and p 23 in micelle form were recovered.

Buoyant density measurements were carried out as described in Example 1 and was found to be 1.22 g $ml^{-1}$ compared to 1.19 g $ml^{-1}$ for the unfragmented surface antigen.

Polyacrylamide gel electrophoresis of the micelles shows that they contain essentially the gp 28 and p 23 polypeptides in the same proportions as the unfragmented surface antigen. Electron microscopy shows the micelles to be roughly spherical in shape and of diameters 140–250 nm. Measurement of over 200 particles indicates an average diameter of 180 nm.

Specific hepatitis B surface antigen activity was monitored by either reverse passive haemagglutination (RPHA) or radioimmunoassay (RIA) throughout the detergent removal steps and no loss of serological activity was detected either after disruption with the Triton or following elution from the Con-A Sepharose. An increase in specific activity has been noticed, perhaps as a result of the removal of new immunoreactive constituents present in the original particle, and at least 70% of the original antigenicity is retained in the micelle preparation. This micelle preparation meets the World Health Organisation requirements in the mouse potency assay test and in the chimpanzee safety and protective tests.

EXAMPLE 3

The procedure described in Example 2 was repeated but using 22 nm particles of surface antigen recovered by the Skelly et al (1978) procedure from the serum of a human carrier. A substantially similar micelle product was obtained as that described in Example 2 except that the buoyant density was found to be 1.24 g $ml^{-1}$ and the micelles were found to be slightly larger (mean diameter 200 nm) compared to the chimpanzee originating material.

I claim:

1. A process for producing a protein fraction suitable for use in the formulation of a vaccine against Hepatitis B virus infection which includes the steps of
    (1) forming an aqueous preparation comprising nonionic detergent and an immunogenic polypeptide obtained either by chemical synthesis or from a genetically engineered host cell and being immunogenically similar to the mixture of polypeptide of molecular weight about 23,000 and glycopolypeptide of molecular weight about 28,000 obtained by treating serum-originating particles of diameter 20 to 25 nm bearing Hepatitis B surface antigen with a non-ionic detergent followed by affinity chromatography, (2) introducing said aqueous preparation to form a layer on top of an aqueous solution buffered to a pH which avoids denaturation of the polypeptide, said aqueous buffer containing sucrose in a concentration gradient of at least 20% to not more than 65% weight/volume, (3) centrifuging the layered buffer and recovering from the buffer an immunogenic aqueous fraction substantially free from detergent and containing micelles of the immunogenic polypeptide.

2. A process according to claim 1 wherein the concentration gradient of the sucrose is at least 20% but not more than 50% weight/volume.

3. A process according to claim 1 wherein the concentration gradient of the sucrose is a linear gradient increasing from 20% up to 50% or 20% up to 60% weight/volume.

4. A process according to claim 1 wherein the sucrose containing aqueous buffer has a pH of 7.0 to 7.5.

5. A process according to claim 1 wherein the sucrose containing aqueous buffer includes sodium phosphate, sodium chloride and ethylene diamine tetra-acetic acid.

6. A process according to claim 1 wherein the detergent containing polypeptide preparation is introduced as a layer on top of the sucrose containing aqueous buffer and the layered buffer centrifuged at a speed corresponding to a force of 40 to 250,000 g.

7. A process according to claim 6 wherein the speed corresponds to a force of at least 200,000 g.

8. A process according to claim 7 wherein the centrifugation is carried out for at least 6 hours at 4° to 20° C.

9. A process according to claim 8 wherein the centrifugation is carried out for about 24 hours.

10. A process according to claim 1 wherein detergent-free micelles of polypeptide are recovered from the centrifuged layered buffer and formulated in a pyrogen-free aqueous medium.

11. A process according to claim 1 wherein the detergent is an aralkyl polyether alcohol.

* * * * *